United States Patent [19]
Ammann et al.

[11] Patent Number: 5,840,058
[45] Date of Patent: Nov. 24, 1998

[54] INFUSION PUMP WITH DISPOSABLE TUBING AND SIZE INDICATING MEANS

[75] Inventors: David Ammann, Alpharetta; Luis Garcia-Verona, Duluth, both of Ga.

[73] Assignee: Alphamed Incorporated, Norcross, Ga.

[21] Appl. No.: 758,967

[22] Filed: Dec. 2, 1996

Related U.S. Application Data

[60] Provisional application No. 60/007,930 Dec. 4, 1995.

[51] Int. Cl.$^6$ ........................................... A61M 1/00
[52] U.S. Cl. ................................. 604/30; 604/131
[58] Field of Search ............................. 604/30, 31–34, 604/131, 151–153, 250–254, 246, 132, 65–67; 128/DIG. 12, DIG. 13

[56] References Cited

U.S. PATENT DOCUMENTS 4,884,065  11/1989  Crouse et al. .
5,531,697   7/1996  Olsen et al. ............................ 604/131
5,531,698   7/1996  Olsen .

*Primary Examiner*—Manuel Mendez
*Attorney, Agent, or Firm*—Michael B. Fein; James A. Drobile

[57] ABSTRACT

A peristaltic infusion pump. According to one embodiment, the pump comprises a tubing set and a pump adapted to receive the tubing set. The tubing set includes an elbow with indicating tabs for indicating the size of the tubing set. The pump determines the size of the tubing set from the indicating tabs on the tubing set.

30 Claims, 13 Drawing Sheets

1000

1050

1100

5,840,058

INFUSION PUMP WITH DISPOSABLE TUBING AND SIZE INDICATING MEANS

CROSS-REFERENCES TO RELATED APPLICATIONS

This non-provisional U.S. national application, filed under 35 U.S.C. § 111(a), claims, under 35 U.S.C. § 119(e)(1), the benefit of the filing date of provisional U.S. national application Ser. No. 60/007,930, filed under 25 U.S.C. § 111(1b) on Dec. 4, 1995, the entirety of which is incorporated herein by reference.

BACKGROUND OF THE INVENTION

1. Field of the Invention

The present invention relates to infusion pumps, and, in particular, to methods and apparatuses for improved peristaltic infusion pumps having disposable tubing sets.

2. Description of the Related Art

Infusion pumps are typically used to deliver fluids, generally pharmaceuticals, nutritionals, or other medication, to patients. A variety of such medication infusion pumps have been employed for the intravenous infusion of medication. Important features of infusion pumps include disposability to prevent cross-contamination, accuracy, safety, ease of use, versatility, and reliability. Peristaltic infusion pumps which function by repetitively compressing a resilient section of tubing with a pump motor are the preferred infusion devices.

Unfortunately, known infusion pumps suffer from a number of disadvantages. In particular, known infusion pumps are relatively limited in the range of infusion rates they are able to accurately achieve. For example, at least two different sizes of infusion pumps are typically required to cover infusion rates from 0.01 ml/hr to 500 ml/hr to accommodate the different tubing sizes necessary to cover the broad range of pumping rates. As a result, there is a need for a single pump adapted to accommodate the different tubing sizes required to cover a broad range of pumping rates. Moreover, any such system should have integral fail-safe mechanisms to ensure that the pump operates at the correct rate for the tubing size placed in the pump. Also, such a system should be adapted to monitor the pressure in the pump tubing, regardless of the tubing size, to detect any downstream occlusion.

In addition, since the tubing typically used in infusion pumps is preferably disposable and, therefore, must be relatively inexpensive, such tubing frequently has minor manufacturing variations that affect the accuracy of the pump. Accordingly, there is a need for an infusion pump capable of identifying and accommodating any manufacturing variations in the tubing.

Infusion pumps should also be equipped with an effective air-in-line detector to prevent embolisms and to notify the user when the medication is not flowing properly through the system. Unfortunately, variations in material, transmissivity, and contamination on the pump tubing may affect the operation of known air-in-line detectors. Accordingly, there is a need for an air-in-line detector capable of compensating for these difficulties.

In addition, many infusion pumps fail to provide adequate free flow prevention devices to restrict the flow of medication when the pump is opened. When the pump is closed and in operation, medication is delivered only at a controlled rate. However, when the pump is opened, there may be no mechanism to prevent flow of medication. In order to prevent free flow of medication, which could result in an overdose, infusion pump operators typically clamp the pump tubing prior to opening the pump. However, if the operator neglects to clamp the tubing, or if the clamp is defective or improperly placed, an overdose may result. As a result, there is a need for a device to automatically prevent the free flow of medication through the pump tubing when the pump is opened.

Finally, infusion pumps must be accurate to ensure that the medications are infused at the proper rate. Typically, desired low flow rates are achieved by halting the infusion pump for periods of time to ensure that the desired average pumping rate is maintained. Unfortunately, many known infusion pumps that employ such a system where, during an off period, the pump is stopped for many minutes, leading to undesirable variations in the medication flow rate. Accordingly, there is a need for an infusion pump with a near constant flow rate.

It is accordingly an object of this invention to overcome the disadvantages and drawbacks of the known art and to provide improved peristaltic infusion pumps.

Further objects and advantages of this invention will become apparent from the detailed description of a preferred embodiment which follows.

SUMMARY OF THE INVENTION

There is provided herein a peristaltic infusion pump. According to one embodiment of the invention, the pump comprises a disposable tubing set and a pump adapted to receive the disposable tubing set. The disposable tubing set includes indicating means for indicating the size of the disposable tubing set. The pump comprises means for determining the size of the disposable tubing set in accordance with the indication of the indicating means.

BRIEF DESCRIPTION OF THE DRAWINGS

Other objects, features, and advantages of the present invention will become more fully apparent from the following detailed description of the preferred embodiment, the appended claims, and the accompanying drawings in which:

DESCRIPTION OF THE PREFERRED EMBODIMENT(S)

Figure 1A:
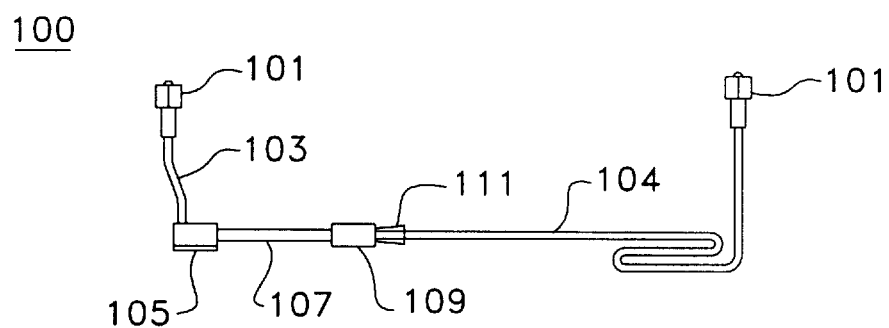
FIGS. 1A–1C show schematic diagrams of various configurations of tube sets for use in an infusion pump in accordance, with the present invention.

An infusion pump in accordance with the present invention comprises one or more disposable sets, a programmable pump unit, one or more additional drone pump units, and a telemetry/charging base. In a preferred embodiment of the present invention, the infusion pump is a peristaltic pump capable of delivering fluids in flow rates ranging from 0.01 ml/hr to 500 ml/hr.

Disposable Tubing Set with Size Indication Means

Referring now to FIGS. 1–5, a disposable tubing set 100 in accordance with a preferred embodiment of the present invention comprises a connector 101, a first tubing segment 103, an elbow body 105, pump tubing 107, an air-in-line detector or sensor piece 109, a free flow preventor 111, a second tubing segment 104, and a second connector 101. Tube sets 100 may come in any number of different sizes. In a preferred embodiment of the present invention, tube sets 100 are made in two sizes, small and large. Tube set size is determined by the size of the pump tubing 107. In addition, a particular pump tubing 107 size may also vary due to imperfections in the manufacturing process for the pump tubing 107. In a preferred embodiment, the small tube set 100 delivers fluids at rates ranging from 0.01 ml/hr to 99.99 ml/hr. The large tube set 100 delivers fluids at rates ranging from 0.1 ml/hr to 500 ml/hr. The connectors 101 may be any connectors suitable for coupling tubing to IV bags, access lines, ports, and the like. The connectors 101 are preferably standard universal connectors used for making such connections. Exemplary connectors 101 include the Luer lock connector and the spike adapter. Adapters tailored for specific applications may also be used.

The first and second tubing segments 103 and 104 are standard medical tubing. The size of the pump tubing 107 is adapted for the desired flow rates. In a preferred embodiment the small tube set 100 has a pump tubing segment 107 approximately 0.075 inches in diameter and the large tube set 100 has a pump tubing 107 segment approximately 0.175 inches in diameter. All tubing 103 and 104 is preferably transparent to permit visualization of the fluid channel.

Figure 2:
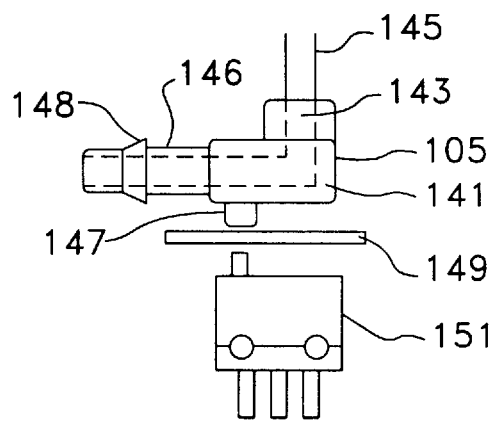
FIG. 2 shows a schematic side view of an elbow and elbow seat switches of an infusion pump in accordance with the present invention.
Figure 3:
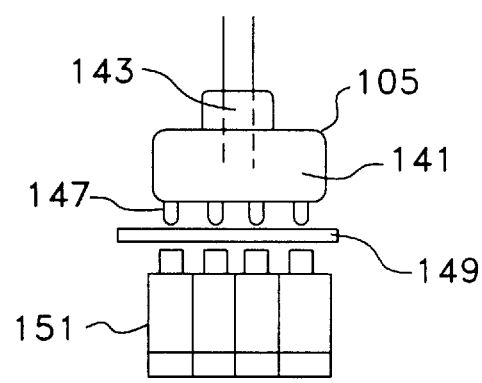
FIG. 3 shows a schematic end view of an elbow and elbow seat switches of an infusion pump in accordance with the present invention.

Referring to FIGS. 2 and 3, the elbow 105 comprises a housing 141 having a channel 143 therethrough and first and second connectors 145 and 146. Since the tube sets 100 come in different sizes, and since the pump tubing 107 has minor size variations within a given size, the elbow 105 further comprises size identification means. In a preferred embodiment, size identification means comprises a pattern of tabs 147 on the bottom of the housing 141. In a preferred embodiment, the elbow 105 has four tab positions. The tabs 147 may be removed or may be molded terminal patterns to identify the size of the tube set 100 as well as any manufacturing variation in the tube set. The pattern of the tabs codes for the size of the tube sets as follows:

| A | B | C | D | |
|---|---|---|---|---|
| 1 | x | x | 0 | Large |
| 0 | x | x | 1 | Small |
| x | 0 | 1 | x | Plus |
| x | 1 | 0 | x | Minus |

Thus, positions A and D code for gross set size and positions B and C code for fine positive or negative size variations caused by any variation in the manufacturing process. The tab pattern is such that a single tab failure can be detected. For example, if a tab at position A is broken off of a large set, it will not be mistakenly indicated that a small set is installed.

Referring now to FIGS. 1–3 and 6A, the elbow body 105 is adapted to fit snugly into the elbow seat 605 of the pump unit such that the tabs rest on and trigger switches 151 in the pump unit 600. The tabs 147 and switches 151 may be separated by a flexible membrane 149 to keep contamination away from the switches 151. The presence of particular tabs 147 conveys tube set 100 size (gross and fine) to the pump 600 by tripping particular switches 151 in the pump unit 600 when the elbow 105 is placed in the elbow seat 605.

The first elbow connector 145 is adapted to couple the first tubing segment 103 to the elbow. The second elbow connector 146 is adapted to couple the elbow 105 to the pump tubing 107. PVC solvent cement is preferably used to secure the 103 and 104 tubing to the elbow connector 145. The second elbow connector 146 preferably has a barb 148 to help secure the pump tubing 107 to the elbow 105. The elbow 105 is preferably transparent to permit the user to visualize the fluid channel. The elbow 105 is preferably made from molded acrylic. The elbow housing 141 preferably has various predetermined protrusions (not shown) on the exterior surface thereof which match cavities (not shown) on the elbow seat 605. The cavities and protrusions ensure proper seating of the elbow housing 141 in the elbow seat 605 and prevent movement of the elbow housing 141 in the elbow seat 605.

The elbow 141 is coupled via second elbow connector 146 to the first end of the pump tubing 107. The pump tubing 107 is flexible tubing, preferably silicone, adapted to be squeezed by the pumping segments 607, which are driven by the pump motor (not shown). The size of the pump tubing 107 determines the flow rate range of the tube set 100. In a preferred embodiment, two sizes of pump tubing 107 are provided in the disposable sets 100. As described above, the small tube set 100 preferably comprises silicone pump tubing 0.075 inches in diameter, and the large tube set 100 preferably comprises pump tubing 0.175 inches in diameter. The length of the pump tubing 107 is adapted to fit into the pump unit 600.

Air-in-Line Sensor

Figure 1B:
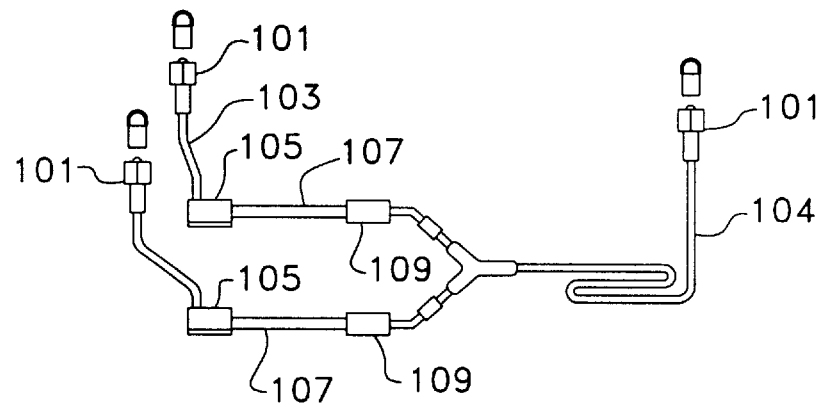
Figure 1C:
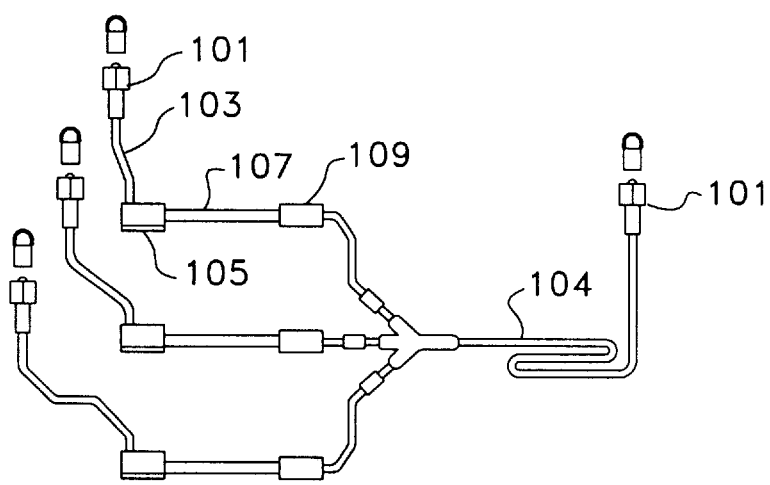
Figure 4:
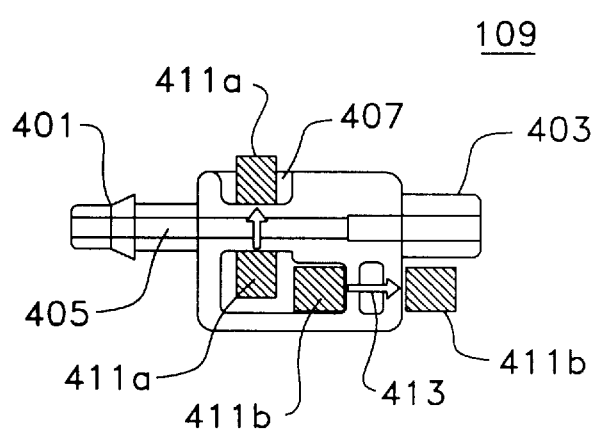
FIG. 4 shows a schematic view of a sensor piece and signal sending and receiving means of an air-in-line sensor in accordance with the present invention.

Referring now to FIGS. 1 and 4, the second end of the pump tubing 107 is coupled to an air-in-line sensor piece 109. The sensor piece 109 comprises first and second connectors 401 and 403, a fluid channel 405 therethrough, first and second cavities 407 and 409 adapted to receive sensor means 411 such as light emitters and detectors, and a reference chamber 413. The sensor piece 109 is adapted to fit into an air-in-line sensor receiving section 611 of the pump unit 600, as illustrated in FIG. 6, which comprises signal sending and receiving means 411. The signal sending means is preferably a light emitter and the signal receiving means is preferably a light detector. In an alternative embodiment, suitable sending and receiving means other than light emitters and detectors may be utilized, such as ultrasonic emitters and detectors.

As illustrated, the first emitter and detector set 411a is arrayed on opposite sides of the fluid channel 405. The second emitter and detector set 411b is arrayed on opposite sides of the reference chamber 413. The reference chamber 413 is filled with air. Light detected by the first detector 411a is compared to light detected by the second or reference detector 411b. If the light is the same, the pump 600 determines that air is in the line. In addition, if the status of the light received by the reference detector 411b changes, the pump 600 determines that a spill may have occurred within the pump unit 900 obscuring the detector 411.

Figure 10A:
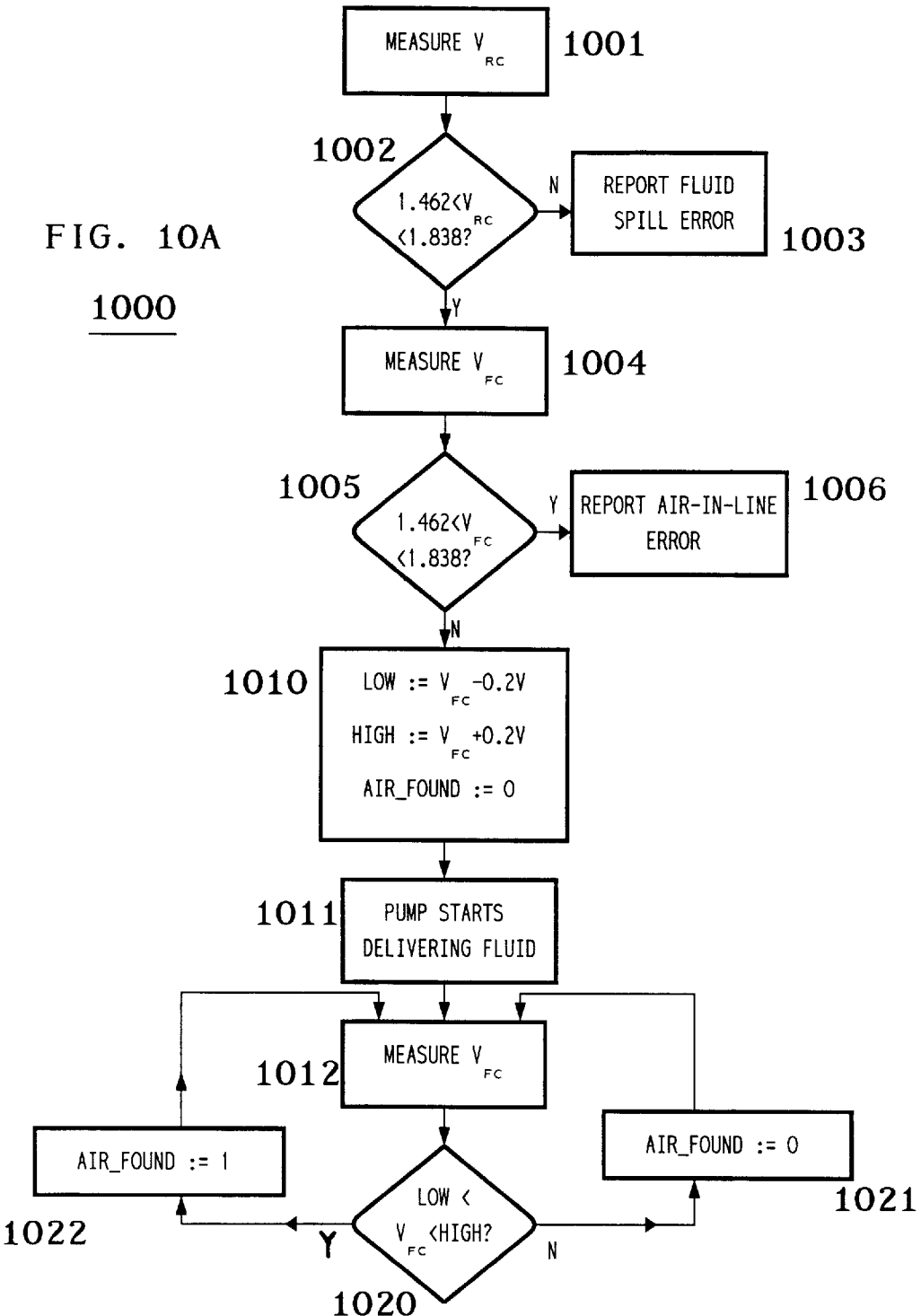
FIGS. 10A–B shows flow diagrams of a method of monitoring the air-in-line sensor of the present invention.
Figure 10B:
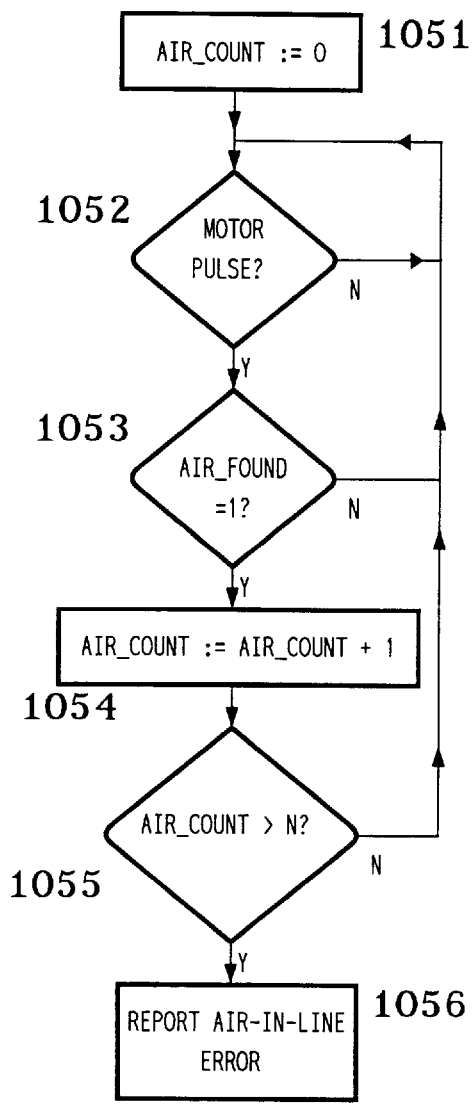

Referring now to FIGS. 10A–B, there is shown flow diagrams 1000, 1050 of a method of monitoring the air-in-line sensor 109 of FIG. 4. Upon power-up the system initializes the air-in-line sensor by checking the reference chamber 413 voltage level VRC (step 1001). If the level is outside a predetermined reference voltage range, a fluid spill may of have occurred and an error is reported (steps 1002, 1003). In a preferred embodiment, the reference voltage range is approximately 1.65V±0.188V, or from 1.462V to 1.838V. If the reference chamber 413 voltage level $V_{RC}$ falls inside this range, then the fluid channel 405 voltage level $V_{FC}$ is measured (steps 1002, 1004). If this voltage $V_{FC}$ is within the reference voltage range 1.65V±0.188V, an AIR-IN-LINE error is reported (steps 1005, 1006). If the fluid channel 405 voltage level is outside the reference voltage, then a LOW and a HIGH variable are initialized based on the fluid channel 405 voltage level, preferably about ±0.20V, creating a "window" around the fluid channel 405 voltage level (steps 1005, 1010). A flag AIR_FOUND is set to 0 (step 1010).

Once the pump starts delivering fluid (step 1011), if the fluid channel 405 voltage level falls inside the range defined by the LOW and HIGH variables (steps 1012, 1020), the AIR_FOUND flag is set to 0 and measurement of $V_{FC}$ continues (steps 1021, 1012). Otherwise, AIR_FOUND is set to 1, and measurement of $V_{FC}$ continues (steps 1022, 1012).

While AIR_FOUND is 1, any motor pulses will be counted by incrementing a variable AIR_COUNT, as illustrated in flow diagram 1050 of FIG. 10B. The variable AIR_COUNT is initially set to 0 (step 1051), and may be reset to 0 periodically, for example once per hour. If there is a motor pulse and the flag AIR_FOUND is 1, then AIR_COUNT is incremented (steps 1052, 1053, 1054). If AIR_COUNT exceeds a maximum value N (step 1055), this indicates that too many motor pulses have occurred while AIR_FOUND is 1 within the predetermined time period (e.g. one hour), and an AIR-IN-LINE error is reported (step 1056).

Free Flow Preventor

Figure 5C:
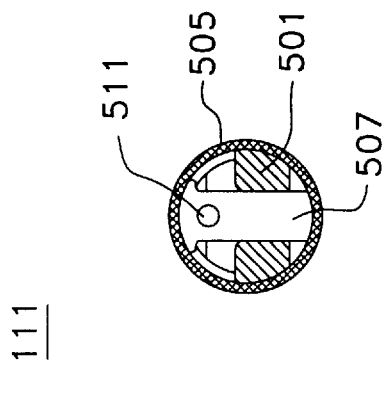
FIGS. 5C–D show a schematic end view of a free flow preventor in accordance with the present invention.
Figure 5D:
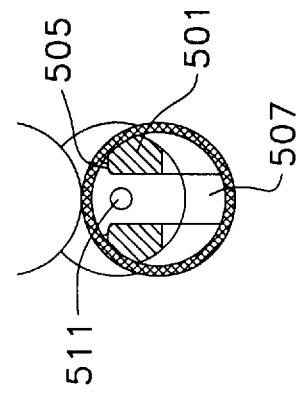
Figure 5A:
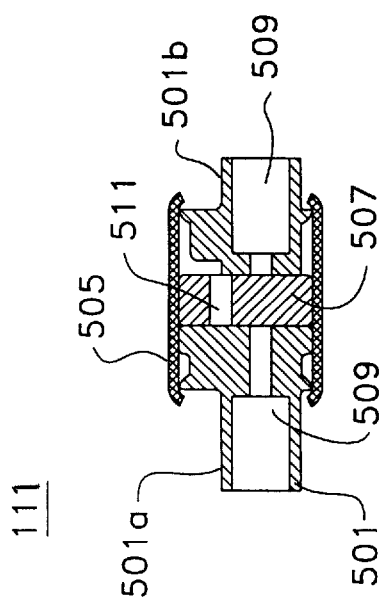
FIGS. 5A–B show a schematic side view of a free flow preventor in accordance with the present invention.
Figure 5B:
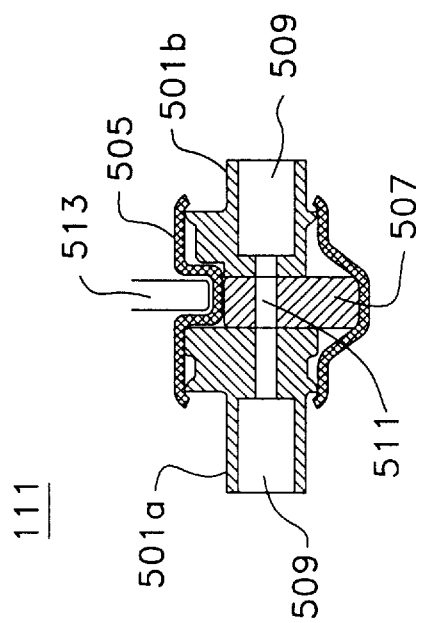

Referring now to FIGS. 1 and 5A–5D the free flow preventor 111 is coupled to the sensor piece 109. As illustrated in FIGS. 5A–5D, free flow preventor 111 comprises a fixed member 501 having first and second ends 501a and 501b and having a fluid channel 509 therethrough. The fixed member 501 is adapted to receive a sliding member 507 also having a channel 511 therethrough. The sliding member 507 is held in the fixed member 501 by an elastic sleeve 505, which preferably consists of silicone tubing. As shown in FIGS. 5A and 5C, when the elastic sleeve 505 is in the undeformed position, the sliding member 507 is positioned so that the channel 511 therethrough is misaligned with the channel 509 through the fixed member 501. As a result, the channel 509 through the fixed member 501 is obstructed. As shown in FIGS. 5B and 5D, when the elastic tubing 505 is deformed, the sliding member 507 is positioned so that the channel 511 through the sliding member 507 aligns with the channel 509 through the fixed member 501, thereby providing an unobstructed fluid channel.

The pump unit 600 is adapted to receive the free flow preventor section 111 such that when the pump unit door is closed and ready for operation a finger 513 coupled to the pump unit door deforms the elastic sleeve 505. Additionally, the elastic sleeve 505 may be deformed manually to permit priming. However, when the pump 600 is opened, the elastic sleeve 505 automatically returns to the undeformed state, thereby closing the fluid channel 509 and preventing free flow. The materials for the fixed and sliding members 501 and 502 are preferably low friction, high tolerance materials such as polypropelene, so as to allow free movement of the sliding member 507 in the fixed member 501 without degradation. The fixed member 501 is preferably transparent to permit visualization of the fluid channel. The sliding member 507 is preferably a contrasting color to permit a human operator to locate and operate the sliding member 507.

Programmable Pump Unit with Pressure Sensor

Referring now to FIG. 6, the infusion pump of the present invention comprises a programmable pump unit 600. The unit comprises a processor section 601 and a disposable set receiving section 603. Disposable set receiving section 603 comprises an elbow seat 605, a pumping section 608, a pressure sensor 609, and an air-in-line sensor receiving section 611.

As described above, the elbow seat 605 is adapted to receive the tube set elbow 105. The elbow seat 605 preferably comprises four micro switches 151 adapted to be triggered by tabs 147 on the elbow 105. The switches 151 are preferably covered by a thin, flexible, rubber membrane 149. The pumping section 608 preferably comprises pumping segments 607 or fingers standard in peristaltic infusion pumps. The pumping section 608 is adapted to receive and act upon the pump tubing 107 of the tube set 100.

Figure 7A:
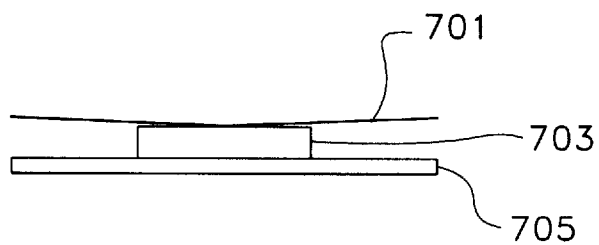
FIG. 7A shows a schematic side view of a pressure sensor in accordance with the present invention.
Figure 7B:
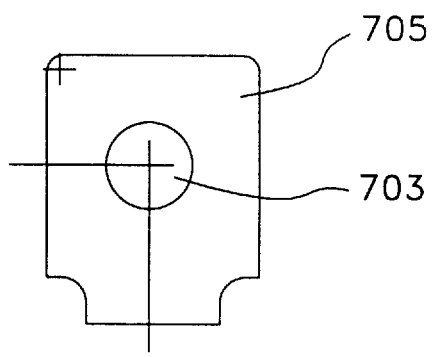
FIG. 7B shows a schematic top view of a pressure sensor in accordance with the present invention.

When placed in the pump unit 600, the pump tubing 107 also is received by pressure sensor 609. Pressure sensor 609 measures the pressure in the tube set 100, which may be used to indicate whether a bag occlusion or a patient side occlusion has occurred. Referring now to FIG. 7, pressure sensor 609 comprises a cover 701, a contact disk 703, and pressure sensor means 705. The cover 701 is preferably made of 5 mil flexible polyester. The contact disk 703 ensures that the contact surface between the pump tubing 107 and the pressure sensor means 705 is constant, regardless of which size tube set 100 is in the pump unit 600 and regardless of whether the pump tubing 107 is slightly misaligned. The contact disk 703 is preferably made of 15 mil rigid polyester. The pressure sensor 705 is preferably a force sensing resistor (FSR), such as that provided by Interlink, Inc. The contact disc 703 is preferably coupled to the cover by an adhesive such as 3M467 Adhesive manufactured by Scotch.

Drone Pump Units

Figure 6A:
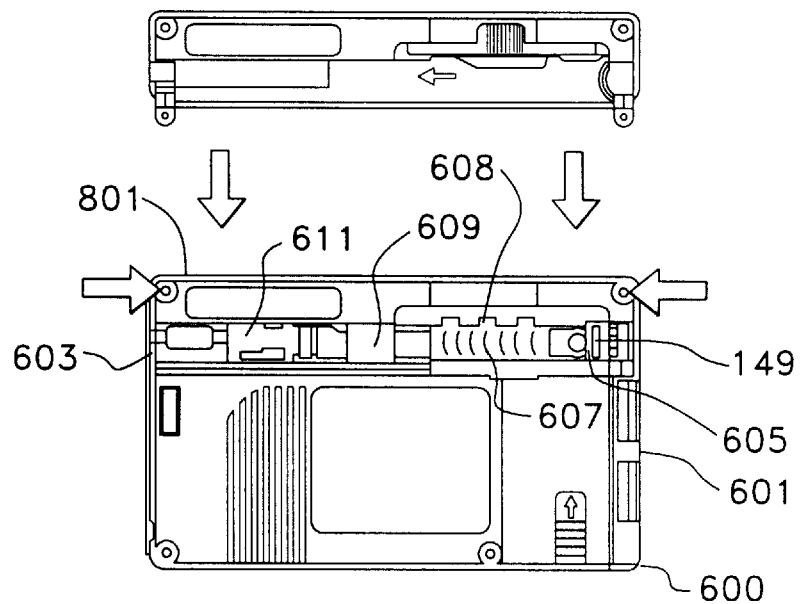
FIGS. 6A–B show a programmable pump unit and drone pump unit in accordance with the present invention.
Figure 8:
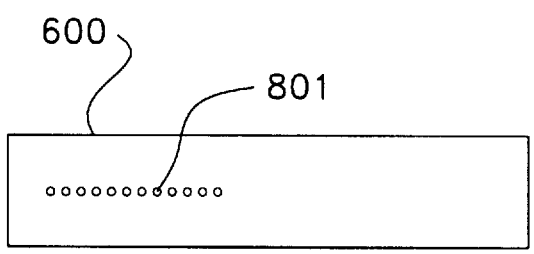
FIG. 8 shows a schematic top view of the adapter means of a programmable pump unit in accordance with the present invention.

Referring now to FIGS. 6A and 8, pumping 600 unit further comprises an expansion port 801. The expansion port 801 is preferably a nine pin port (3 voltage lines, 2 communications lines, 1 control line, 2 ground lines, and 1 safety/termination line). The voltage lines provide power to an attachable drone pumping unit 613. The control line provides control over a variable power supply for the motor. This power supply preferably provides two voltages: battery voltage (2.2 VDC–3.2 VDC) or 5 VDC. The variable voltage allows better motor control and flowrate range. The safety/ termination line carries a signal to the programmable pump 600 to terminate the pump motor and trigger the alarm if an error, either hardware or software, is detected. The data lines allow the pump to communicate with the drone units 613.

Figure 6B:
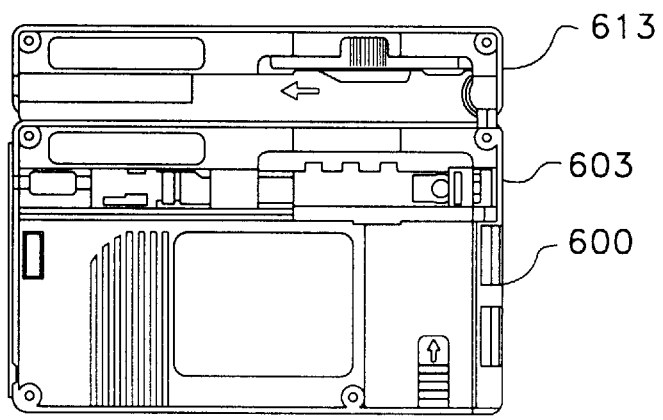

An infusion device in accordance with the present invention therefore preferably comprises one or more drone pumping units 613. Referring now to FIGS. 6A, 6B and 8, the programmable pump unit 600 (PPU) may be coupled to additional drone pumping units 613 by means of the expansion port 801 described above. Each drone pumping 613 unit has a pumping section (not shown) identical to the pumping section 603 in the PPU 600. In addition, each drone unit 613 has both a male and female 9 pin port. Accordingly, a drone unit 613 may be attached directly to the PPU 600 or to another drone unit 613 (not shown). As each drone 613 is attached, the PPU 600 receives a signal from the drone 613 and allows the user to program the drone 613 pumping channel in addition to the original pumping channel 603 provided in the PPU 600.

Base Unit

Figure 9:
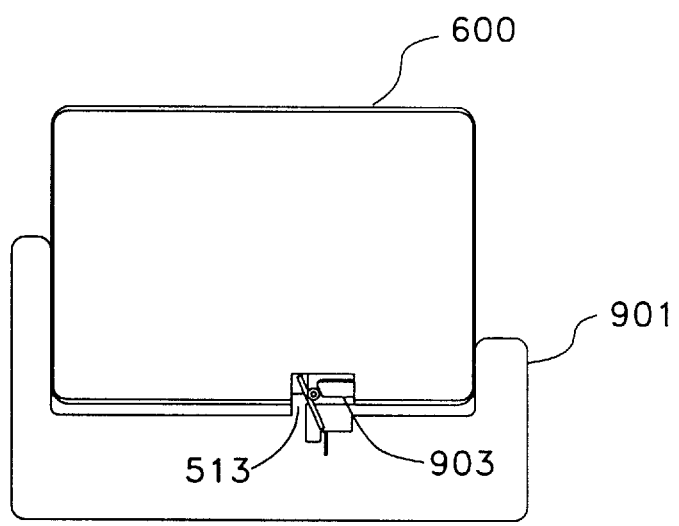
FIG. 9 shows a schematic side view of a programmable pump unit resting in a base unit in accordance with the present invention.

Referring now to FIG. 9, there is shown a schematic side view of a programmable pump unit 600 resting in a charging/telemetry base unit 901 in accordance with a preferred embodiment of the present invention. Base 901 preferably comprises a modem, phone jack, and battery charging means (not shown). The base 901 allows a remote personal computer (PC) (not shown) to monitor and/or to update, either directly or through a modem, the pump status and the pump's user program. In addition, the pump's history records may be disembodied to the PC for record keeping and further analysis. The base 901 is adapted to receive the programmable pumping unit as described above. In a preferred embodiment, the base has a finger 513 adapted to automatically open the data/charging port 903 of the PPU 600.

Means for Monitoring and Controlling Flow Rate

Figure 11A:
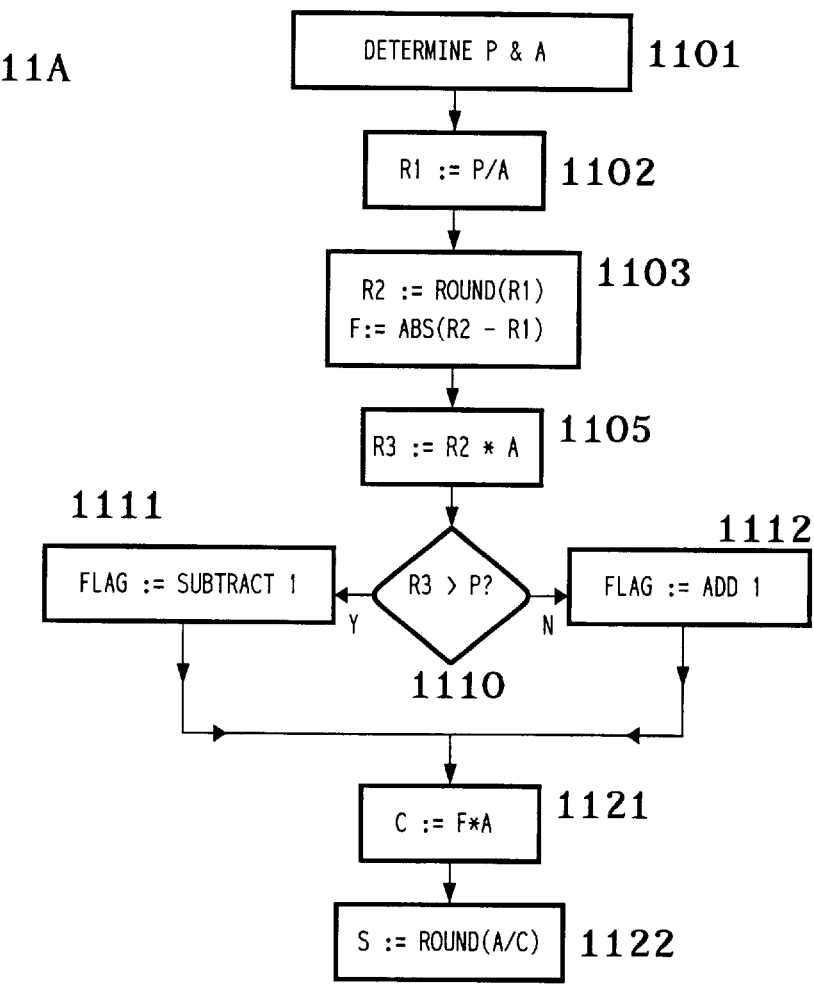
FIGS. 11A–B shows flow diagrams of a method for controlling the flow rate of an infusion pump in accordance with a preferred embodiment of the present invention.

In order to provide the most accurate flow rate using the least amount of energy, art infusion pump in accordance with the present invention operates by activating the pump motor repeatedly for small time periods. In a preferred embodiment of the present invention, the pump motor is activated every five seconds. Thus, every five seconds, there is an activation period (of no more than five seconds) during which the pump applies a consecutive series of pulses to the pumping segments 607 of pumping section 608, which act upon pump tubing 107 of tube set 100. In order to deliver the desired flow rate, the pump first determines the number of pulses P necessary to deliver the desired volume, since each pulse causes a known quantity of volume to be delivered. The total number of pulses is dependent upon the size of the pump tubing 107. The pump then determines the number of pulses to be delivered during each activation period in accordance with the following steps, which are illustrated in flow diagram 1100 of FIG. 11A.

First, the total number of pulses P and number of activation periods A in a fixed time period T are determined (step 1101). For example, if activation periods occur every five seconds,, there are 720 activation periods (A) in one hour (T). Next, the pump divides the number of pulses P by the number of activation periods A to yield result $R_1$ (step 1102). $R_1$ represents the average number of pulses that should be generated per activation period to provide a total of P pulses. However, $R_1$ is a real number, and it is not possible to actually provide a fraction of a pulse in an activation period. Thus, result $R_2$ is determined by rounding real number $R_1$ to the nearest integer, and a fractional component F is determined by taking the absolute value of the difference between $R_2$ and $R_1$ (step 1103).

Since $R_2$ is a rounded number, generation of exactly $R_2$ pulses for each of A activation periods will usually result in a total number of pulses different than P during time T. Thus, result $R_3$, the product of rounded number $R_2$ and A, is computed (step 1105). $R_3$ represents the total number of pulses that would be delivered if the rounded number $R_2$ is used to supply $R_2$ pulses per activation period. If $R_3$ is greater than P, then a flag is set to "subtract 1" (steps 1110, 1111). Otherwise, if $R_3$ is less than P, then a flag is set to "add 1" (steps 1110, 1112). During generation of pulses, as described below with reference to flow diagram 1150 of FIG. 11B, some of the activation periods are "corrective activation periods" in which either $R_2-1$ or $R_2+1$ pulses will be generated rather than $R_2$ pulses, depending upon whether the flag has been set to "subtract 1" or "add 1". Activation periods in which either $R_2-1$ or $R_2+1$ pulses are generated are referred to as "corrective activation periods." Activation periods in which exactly $R_2$ pulses are generated may be referred to simply as activation periods or as "normal activation periods."

After the flag is set in steps 1111 or 1112, a value C is calculated as the product of F and A (step 1121), where C is the optimal number of corrective activation periods. It is desirable to ensure as even a distribution of pulses as possible by more or less evenly distributing the corrective activation periods among the normal activation periods. Thus, in step 1122, value S is determined as the rounded value of (A/C), where S is a skip value that indicates how often to have a corrective activation period. Thus, if S is 3, every $S^{th}$ activation period will be a corrective activation period in which the number of pulses generated is either $R_2-1$ or $R_2+1$ depending, respectively, upon whether the flag was set to "subtract 1" or "add 1."

A numerical example of the operation of the above-described steps of flow diagram 1100 is provided as follows. The infusion pump of the present invention may be used to deliver 1 ml of medication per hour, with a tube set that requires 53,000 pulses P to deliver 1 ml of fluid, with activation periods every 5 seconds. Thus, P is 53,000 and A is 720 (step 1101). Result $R_1$ (P/A) is 73.611 (step 1102). Result $R_2$ (Round(73.611)) is determined to be 74, and F is 0.389 (step 1103). $R_3$, the product of rounded number $R_2$ and A, is computed to be 53,280 pulses (step 1105). As will be appreciated, without the error correction provided by the use of corrective activation periods, the pump would deliver a pulse rate of 74 pulses every 5 seconds which would yield 53,280 pulses per hour for an error rate of 0.52%. Since 53,280 is greater than P (53,000), the flag is set to subtract 1 (steps 1110, 1111). This indicates that during corrective activation periods, 1 is subtracted from the number $R_2$ (74) of pulses that are delivered during normal activation periods.

Value C is calculated as the product of F and A to be 280 (step 1121), as explained above. Value S is determined as the rounded value of (A/C), or round(720/280)=round(2.57)=3 (step 1122). Thus, every third activation period will be a corrective activation period in which the number of pulses generated is $R_2-1$, since the flag was set to "subtract 1" in step 1111 in this example. Thus, in the present example, for 480 (normal) activation periods, the number of pulses generated will be 74 per activation period, and for 240 activation periods, the number of pulses generated will be 73 per activation period. The total number of pulses generated after 720 activation periods will therefor be: (480×74)+(240×73)=35,520+17,520=53,040, providing an error rate of +0.075%.

Figure 11B:
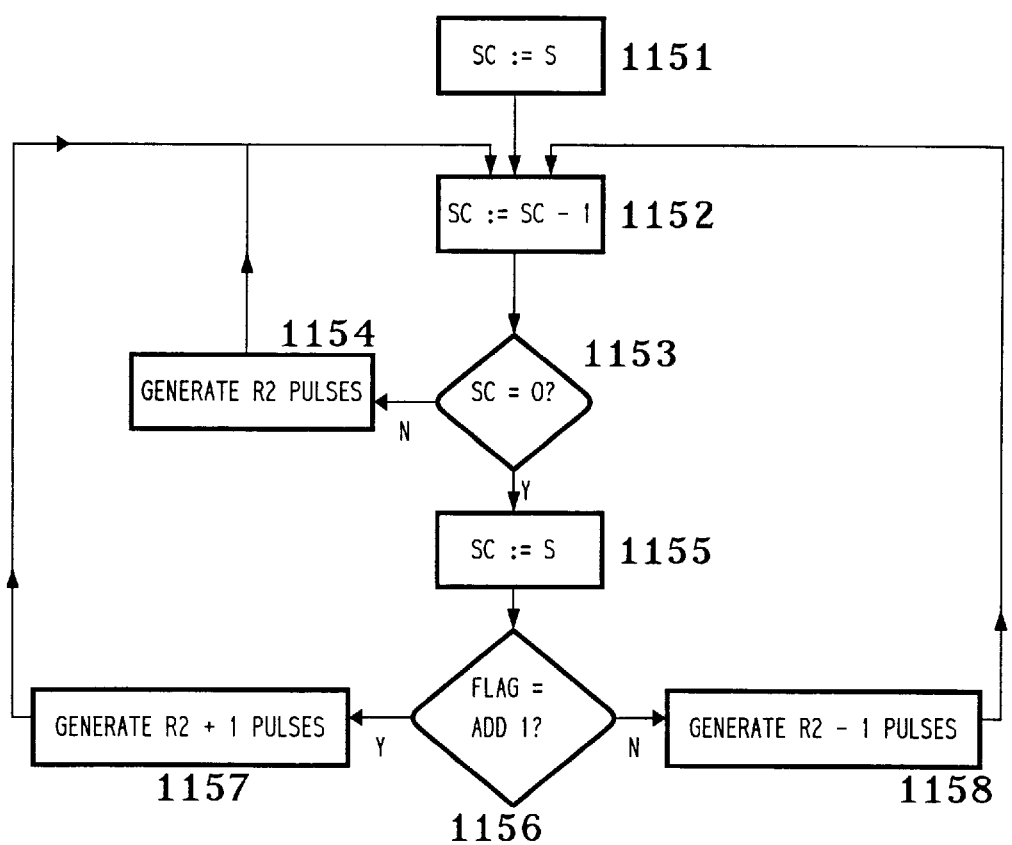

Referring now to FIG. 11B, there is shown flow diagram 1150 of a method for controlling the flow rate of an infusion pump in accordance with a preferred embodiment of the present invention. Utilizing the results generated from flow diagram 1100 of FIG. 11A, the pump initially sets a variable SC to S (step 1151). Steps 1152–1158 are then repeated A times, once per each activation period. In each loop of steps 1152–1158, either $R_2$, $(R_2-1)$, or $(R_2+1)$ pulses are generated, depending upon whether there current activation period is determined to be a normal or corrective activation period and depending upon whether the flag is set to add 1 or subtract 1.

Thus, using the numerical examples given above, SC is initially set to 3 (step 1151). Entering the loop, SC is decremented (step 1152) and checked to see if it has reached 0 yet (step 1153). If not, the activation period is a normal activation period and 74 pulses are generated, and the loop repeats (step 1154). If SC=0, SC is once more initialized to S, and the flag is checked to see whether it has been set to "add 1" or not (steps 1153, 1155, 1156). In this case, the flag is not set to "add 1", since it has been set to "subtract 1". Thus, 73 pulses are generated (steps 1156, 1158), and the loop is repeated (step 1152).

It will be understood that various changes in the details, materials, and arrangements of the parts which have been described and illustrated in order to explain the nature of this invention may be made by those skilled in the art without departing from the principle and scope of the invention.

What is claimed is:

1. An apparatus, comprising:
   (a) a tubing set comprising flexible pump tubing of a size adapted for a specific flow rate, a housing having a fluid channel therethrough and comprising size identification means, the size identification means adapted to identify the flexible pump tubing size, and the housing permanently connected to the flexible pump tubing; and
   (b) a pump adapted to receive the housing and the flexible pump tubing portion of the tubing set, the pump comprising means for reading the identification means on the housing when the housing and the flexible tubing are received within the pump.

2. The apparatus of claim 1, wherein the pump is a peristaltic infusion pump for the intravenous infusion of medication and the tubing set is a disposable tubing set.

3. The apparatus of claim 2, wherein the tubing set comprises transparent tubing.

4. The apparatus of claim 1, wherein the tubing set is one of a small tubing set and a large tubing set.

5. The apparatus of claim 4, wherein:
   the small tubing set comprises pump tubing of about 0.075 inches in diameter and is adapted to deliver fluids at rates ranging from 0.01 ml/hr to 99.99 ml/hr; and
   the large tubing set comprises pump tubing of about 0.175 inches in diameter and is adapted to deliver fluids at rates ranging from 0.1 ml/hr to 500 ml/hr.

6. The apparatus of claim 1, wherein the size identification means on the housing comprises a plurality of tab positions.

7. The apparatus of claim 6, wherein:
   the plurality of tab positions comprises four tab positions including first, second, third, and fourth tab positions;
   the first and fourth tab positions code for gross tubing set size; and
   the second and third tab positions code for fine positive or negative tubing set size variations;
   whereby a single tab position failure can be detected.

8. The apparatus of claim 6, wherein the means for reading the identification means on the housing comprises a plurality of switches within the portion of the pump adapted to receive the housing and the flexible pump tubing portion of the tubing set, each of which switch is for detecting whether or not a tab is present in a corresponding tab position of the plurality of tab positions on the housing.

9. The apparatus of claim 8, wherein:
   the housing is an elbow body which comprises the plurality of tab positions; and
   the pump comprises an elbow seating means for securably coupling the elbow body to the pump and for operatively coupling the plurality of tab positions to the plurality of switches.

10. The apparatus of claim 1, wherein:
    the tubing set comprises an elbow body which comprises the indicating means; and
    the pump comprises an elbow seating means for securably coupling the elbow body to the pump.

11. A method, comprising:
    (a) providing a tubing set comprising flexible pump tubing of a size adapted for a specific flow rate, a housing having a fluid channel therethrough and comprising size identification means, the size identification means adapted to identify the flexible pump tubing size, and the housing permanently connected to the flexible pump tubing;
    (b) providing a pump adapted to receive the tubing set;
    (c) indicating with indicating means of the housing the size of the flexible pump tubing; and
    (d) determining with size determining means of the pump the size of the flexible pump tubing from the indicating means on the housing.

12. The method of claim 11, wherein the pump is a peristaltic infusion pump for the intravenous infusion of medication and the tubing set is a disposable tubing set.

13. The method of claim 12, wherein the tubing set comprises transparent tubing.

14. The method of claim 11, wherein the tubing set is one of a small tubing set and a large tubing set.

15. The method of claim 14, wherein:
    the small tubing set comprises pump tubing of about 0.075 inches in diameter; and
    the large tubing set comprises pump tubing of about 0.175 inches in diameter; the method comprising the further steps of:
    delivering fluids with the small tubing set at rates ranging from 0.01 ml/hr to 99.99 ml/hr; and
    delivering fluids with the large tubing set at rates ranging from 0.1 ml/hr to 500 ml/hr.

16. The method of claim 11, wherein the indicating means comprises a plurality of tab positions.

17. The method of claim 16, wherein:
    the plurality of tab positions comprises four tab positions including first, second, third, and fourth tab positions;
    the first and fourth tab positions code for gross tubing set size; and
    the second and third tab positions code for fine positive or negative tubing set sure variations;
    whereby a single tab position failure can be detected.

18. The method of claim 16, wherein the size determining means comprises a plurality of switches, each of which is for detecting whether or not a tab is present in a corresponding tab position of the plurality of tab positions.

19. The method of claim 18, wherein:
    the housing is an elbow body which comprises the plurality of tab positions; and the pump comprises an elbow seating means for securably coupling the elbow body to the pump and for operatively coupling the plurality of tab positions to the plurality of switches.

20. The method of claim 11, wherein:

the tubing set comprises an elbow body which comprises the indicating means; and the pump comprises an elbow seating means for securably coupling the elbow body to the pump.

21. An apparatus comprising a tubing set for use with a pump adapted to receive the tubing set, wherein the tubing set comprises flexible pump tubing of a size adapted for a specific flow rate, a housing having a fluid channel therethrough and comprising size identification means, the size identification means adapted to identify the flexible pump tubing size, and the housing permanently connected to the flexible pump tubing the tubing set adapted for use with a pump which comprises size determining means for determining the size of the tubing set from the indicating means on the housing.

22. The apparatus of claim 21, wherein the pump is a peristaltic infusion pump for the intravenous infusion of medication and the tubing set is a disposable tubing set.

23. The apparatus of claim 22, wherein the tubing set comprises transparent tubing.

24. The apparatus of claim 21, wherein the tubing set is one of a small tubing set and a large tubing set.

25. The apparatus of claim 24, wherein:

the small tubing set comprises pump tubing of about 0.075 inches in diameter and is adapted to deliver fluids at rates ranging from 0.01 ml/hr to 99.99 ml/hr; and the large tubing set comprises pump tubing of about 0.175 inches in diameter and is adapted to deliver fluids at rates ranging from 0.1 ml/hr to 500 ml/hr.

26. The apparatus of claim 21, wherein the indicating means comprises a plurality of tab positions.

27. The apparatus of claim 26, wherein:

the plurality of tab positions comprises four tab positions including first, second, third, and fourth tab positions;

the first and fourth tab positions code for gross tubing set size; and the second and third tab positions code for fine positive or negative tubing set size variations;

whereby a single tab position failure can be detected.

28. The apparatus of claim 26, wherein the size determining means of the pump comprises a plurality of switches, each of which is for detecting whether or not a tab is present in a corresponding tab position of the plurality of tab positions.

29. The apparatus of claim 28, wherein:

the tubing set comprises an elbow body which comprises the plurality of tab positions; and the pump comprises an elbow seating means for securably coupling the elbow body to the pump and for operatively coupling the plurality of tab positions to the plurality of switches.

30. The apparatus of claim 21, wherein:

the tubing set comprises an elbow body which comprises the indicating means; and the pump comprises an elbow seating means for securably coupling the elbow body to the pump.

* * * * *